(12) United States Patent
Levin et al.

(10) Patent No.: US 8,409,445 B2
(45) Date of Patent: Apr. 2, 2013

(54) METHOD FOR REMOVING GASES FROM A CONTAINER HAVING A POWDERED CONCENTRATE FOR USE IN HEMODIALYSIS

(75) Inventors: Roland Levin, San Ramon, CA (US); Wayne Raiford, Fairfield, CA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 564 days.

(21) Appl. No.: 12/626,348

(22) Filed: Nov. 25, 2009

(65) Prior Publication Data

US 2011/0120946 A1    May 26, 2011

(51) Int. Cl.
*B01D 61/26* (2006.01)
*B01D 61/32* (2006.01)
*B01D 19/00* (2006.01)

(52) U.S. Cl. ........ 210/741; 210/645; 210/739; 210/744; 95/19; 95/241

(58) Field of Classification Search ............... 210/85, 210/86, 90, 97, 109, 120, 137, 143, 175, 210/188, 252, 257.1, 258, 436, 472, 645, 210/646, 718, 739, 741, 744; 95/19, 24, 95/241
See application file for complete search history.

(56) References Cited

U.S. PATENT DOCUMENTS

| | | | |
|---|---|---|---|
| 4,770,769 A | 9/1988 | Schael | |
| 5,385,564 A | 1/1995 | Slater et al. | |
| 5,460,446 A | 10/1995 | Chevallet et al. | |
| 5,511,875 A | 4/1996 | Jonsson et al. | |
| 5,616,305 A | 4/1997 | Mathieu | |
| 5,727,877 A | 3/1998 | Chevallet et al. | |
| 7,223,262 B2 | 5/2007 | Brehm et al. | |

FOREIGN PATENT DOCUMENTS

| | | |
|---|---|---|
| DE | 41 13 032 A1 | 11/1991 |
| DE | 103 13 965 B3 | 10/2004 |
| EP | 0 714 668 A1 | 6/1996 |
| WO | 2008/065470 A1 | 6/2008 |

OTHER PUBLICATIONS

English translation of German Patent Application No. DE 41 13 032 A1 (Nov. 1991).*

* cited by examiner

*Primary Examiner* — John Kim
(74) *Attorney, Agent, or Firm* — Leydig, Voit & Mayer, Ltd.

(57) ABSTRACT

An apparatus and a method for filling a container containing a dry powdered salt concentrate for use in dialysis with purified fluid and removing the trapped air or gases generated during the filling of the container, while maintaining the required fluid level in the container and without the need for evacuating gases from the container prior to filling.

12 Claims, 5 Drawing Sheets

METHOD FOR REMOVING GASES FROM A CONTAINER HAVING A POWDERED CONCENTRATE FOR USE IN HEMODIALYSIS

BACKGROUND OF THE INVENTION

Dialysis is performed as a treatment for patients suffering from renal insufficiency. Dialysis can be performed either in the peritoneum, or through extracorporeal dialysis or filtration of blood. These two dialysis methods have in common the fact that dialysis fluids or dialysates take up the degradation products of metabolism. These dialysates usually contain high levels of sodium chloride and other electrolytes, such as calcium chloride, or potassium chloride, a buffer substance, such as bicarbonate, or acetate and acid to establish a physiological pH, plus optionally, glucose or another osmotic agent.

Dialysates are either supplied as ready-to-use solutions or they are prepared on site from concentrates, including solid concentrates. Solids offer the advantage of a small package volume and a low weight. Although solids also have disadvantages—electrolyte salts, for example, are highly hygroscopic—there is a trend toward offering only solid components for preparation of dialysates.

In the above mentioned hemodialysis systems, a flexible bag or container filled with a powdered salt concentrate is used to generate a concentrated salt solution. Purified fluid is added to the top of the container and the concentrated solution is removed from the bottom of the container. When the concentrated solution is removed from the bottom of the bag it is generally delivered to the hemodialysis machine for use in the dialysate. It is important that the fluid level in the container with the salt concentrate is maintained above the level of the salt in the container, when the solution is being pumped out of the bottom of the container. Under normal operation, the fluid level above the powdered salt layer is maintained or increases as the salt concentrate is consumed. However, if the fluid level falls below the level of the salt concentrate, air or gases in the bag may be pumped through the salt concentrate and out of the bottom of the container into the dialysate.

During hemodialysis, using systems such as described in U.S. Pat. No. 5,385,564 and U.S. Pat. No. 5,616,305, incorporated by reference herein, dry bicarbonate or acid concentrate is mixed with dialysate via a container using one or more ports. Even when the container is filled there is always air remaining in the container. The system cannot remove all of the air from the container without evacuating the air from the container via a vacuum system to create negative pressure, before filling the container with fluid.

To deter air from being drawn into the hydraulics of the machine during operation, it is desirable to fill the container with a sufficient volume or fluid to maintain a fluid layer above the dry powder. In the systems known in the art, without removing air from the bag via a vacuum, some containers will not maintain the correct fluid layer, and thus, extra air passes into the hydraulics which requires excessive venting procedures. The new method and arrangement of the present invention solves the problem without the need to generate a vacuum to evacuate the gases from the concentrate.

BRIEF SUMMARY OF THE INVENTION

In an embodiment, the present invention provides a system and a method for filling a container containing a dry powdered salt concentrate with purified fluid for use with a dialysis apparatus. According to a disclosed method, the trapped air or gases generated during the filling of the container are forced out of the container without the creating a vacuum in the container prior to filling.

According to a disclosed method, fluid is rapidly pumped into a container having a dry powdered salt concentrate. When the interior of the container reaches a first pressure, contents of the container, including residual and generated gases as well as some fluid, are permitted to flush from the container, and out eventually out of the system. During this flushing step, adequate fluid is provided to maintain the first pressure within the container. At the conclusion of the flushing step, the pressure in the container is reduced to a second, lower operating pressure, and the system begins regular operation with delivery of solution to the dialyzer. According to various embodiments, the flushing step may proceed for a set time, or until such time a given level of air is no longer detected in the solution leaving the container for a given period of time.

In another embodiment, the present invention also provides a system for removing gases from a container having a powdered salt concentrate for use in a dialysis apparatus. The system further includes a fluid source, a pump which is in fluid communication with the fluid source, at least one hydraulic line having one end in fluid communication with the fluid supply and a second end in fluid communication with a drain. The system further includes a bypass valve that is disposed downstream from the first pump and upstream from the inlet of the container. The valve is capable of directing fluid flow into the hydraulic line or into the container. An outlet of the container is in fluid communication with the hydraulic line downstream from the bypass valve. A pressure sensor monitors the pressure of the fluid pressure in the container.

In an embodiment, a second valve is provided downstream the container to facilitate pressurization of the container. In another embodiment an air sensor is provided to detect gases in the solution flowing from the container.

DETAILED DESCRIPTION OF THE INVENTION

For the purposes of this disclosure, the term "operating pressure" means the fluid or fluid pressure in the container having a powdered salt concentrate, during operation of the system, where the system is capable of supplying a concentrated salt solution to the dialysis apparatus. The term "flushing step" means operating the system to remove trapped gases from a container having a powdered salt concentrate, by pumping fluid through the container at a pressure that is greater than the operating pressure of the system, and directing the outflow out of the system to a drain, instead of to a dialysis apparatus.

Figure 1:
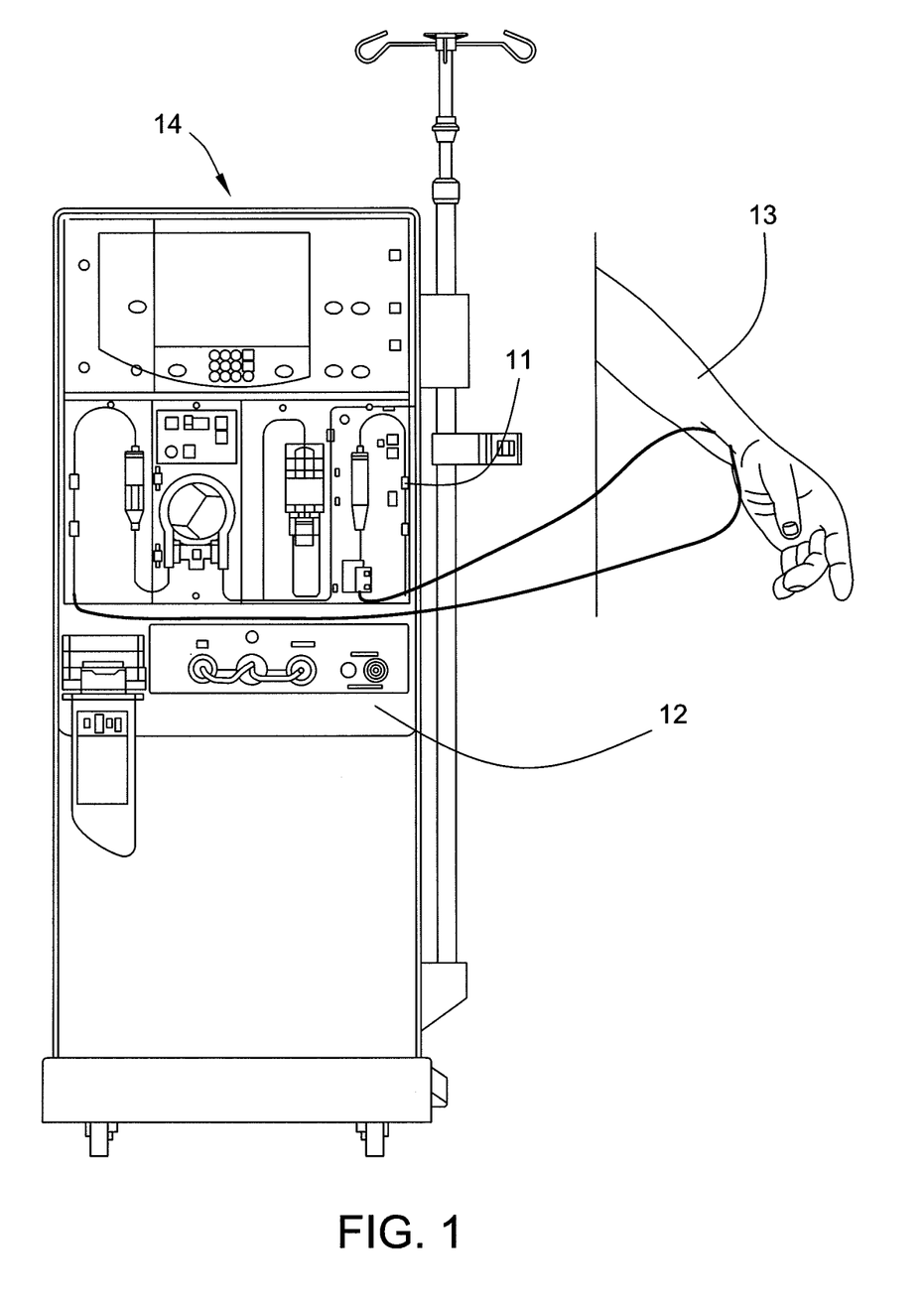
FIG. 1 is a schematic diagram the general environment where the system is operating. A patient is shown attached to a dialysis apparatus. It is understood that the system of the present invention supplies dialysate solution to such an apparatus for use in hemodialysis.

Turning now to the drawings, FIG. 1 displays the general context of a dialysis system 10. The dialysis system 10 includes the dialyzer 11, and a subsystem 12 for preparing a salt solution from a powdered salt concentrate for use in the dialyzer 11. The salt solution is provided to the dialyzer 11 for administration to a patient 13. The dialysis system 10 may additionally include various other optional subsystems and equipment.

Figure 2:
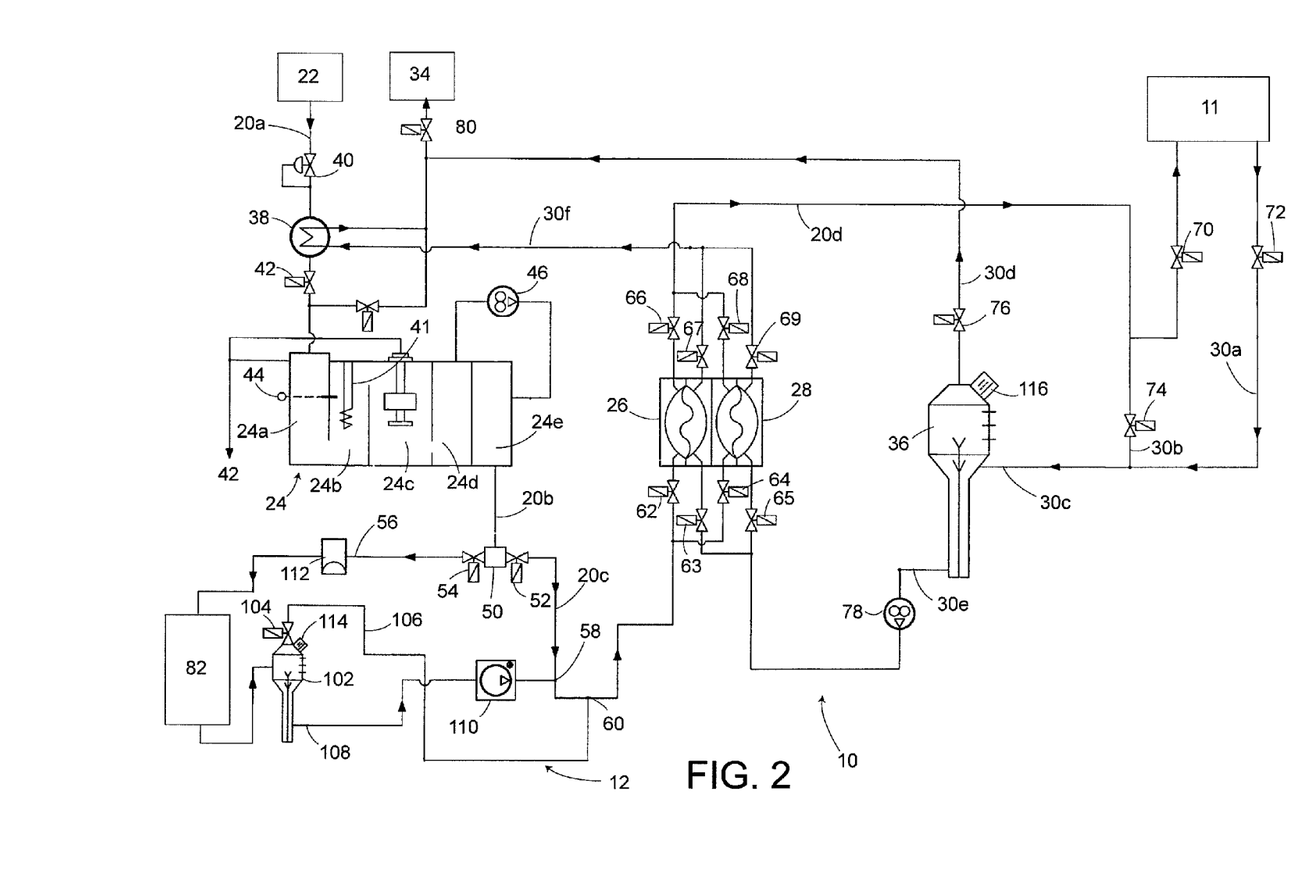
FIG. 2 is a schematic diagram of an embodiment of a system for the production and discharge of a liquid hemodialysis concentrate for use in a dialysis apparatus.

FIG. 2 illustrates a representative hydraulic arrangement of the dialysis system 10. By way of a general overview of the operation, the system 10 includes a main hydraulic line 20a-d that is fluidly coupled to a fluid source 22 at one end, and to the dialyzer 11 at the other end, with various optional assemblies disposed along the mainline 20. It is noted that the mainline 20a-d may include a plurality of hydraulic lines. In the illustrated embodiment, optional assemblies are disposed along the mainline 20 in addition to the subsystem 12 for preparing a salt solution and may include a hydroblock 24 and one or more balancing chambers 26, 28. A return line 30a-f from the dialyzer 11 provides return flow from the dialyzer 11 to a drain 34. As with the mainline, the return line 30a-f may include a plurality of hydraulic lines. Subassemblies such as an air separation chamber 36 or a heat exchanger 38 may be provided along the return line 30. It is noted that not all elements of the illustrated hydraulic arrangement are necessary to the structure and operation of the subsystem 12 for preparing a salt solution from a powdered salt concentrate, although a general explanation is provided herein in the interest of completeness.

Turning now to the specifics of the illustrated hydraulic arrangement, the fluid source 22 may include any appropriate type of fluid or fluids. For example, a reverse osmosis fluid (RO fluid) source may be provided. It will be appreciated that an alternate fluid may be provided as required by the system 10. While the fluid referenced in this disclosure will be fluid, it is intended that the terms "fluid" and "fluid" will encompass other appropriate fluids for the purposes of the disclosed method and arrangement.

Fluid from the fluid source 22 flows through mainline 20a to the hydroblock 24. In this embodiment, the heat exchanger 38, a pressure regulator 40, and a control valve 42 are provided along the mainline 20a between the fluid source 22 and the hydroblock 24. While the valve 42 controls overall flow to the mainline 20a, the pressure regulator 40 may control the pressure of the fluid as it passes through this section of the mainline 20a. The heat exchanger 38 may heat the fluid somewhat with heat from the return spent fluid, as will be discussed below.

The illustrated hydroblock 24 is a multichambered unit, the fluid being heated by a heater 41 in chamber 24b and vented to a vent 42 in chamber 24c as the fluid flows through the various chambers 24a-e of the hydroblock 24. The fluid temperature within the hydroblock 24 may be monitored and/or controlled by a control thermostat 44. A deaeration pump 46 pumps fluid between the forth and fifth chambers 24d, 24e of the hydroblock 24 to return the fluid to the mainline 20b.

Leaving the hydroblock 24, the mainline 20b bifurcates at a branch point 50. Valves 52, 54 control the flow of fluid to the continuing mainline 20c and a subsystem line 56, respectively. If the valve 54 is closed and valve 52 open, the fluid continues through the valve 52 to the mainline 20c. If the valve 54 is open and the valve 52 closed, fluid proceeds through valve 54 to the subsystem line 56. As with all of the valves in this disclosure, the valves 52, 54 may be simple shut-off valves, or other multiposition valves. For example, valves 52, 54 may be replaced by a single valve that includes positions that arrest flow entirely, that direct flow to the subsystem line 56, or that direct flow along the mainline 20c.

Returning to FIG. 2, the subsystem line 56 connects flow from the mainline 20b to the subsystem 12 for preparing a salt solution, as will be explained in greater detail below. After leaving the subsystem 12, the salt solution is returned to the mainline 20c at least one of junction 58 or 60. The continuing mainline 20c directs flow to the balance chambers 26, 28, flow through the balancing chambers 26, 28 being controlled by a plurality of valves 62-69. Each of the balancing chambers 26, 28 includes two separate subchambers separated by a flexible membrane, the significance of which will be discussed below. Flow from the subsystem 12 flows into the respective balancing chambers 26, 28 through valves 62 and 64, and out from the balancing chambers 26, 28 through valves 66, 68.

Leaving the balancing chambers 26, 28, the fluid from the subsystem 12 is directed through mainline 20d. Flows to and from the dialyzer 11 are controlled by a pair of control valves 70, 72 disposed along the mainline 20d and the return line 30a, respectively. Thus, fluid from the balancing chambers 26, 28 flowing through mainline 20d moves on to the dialyzer 11 when dialyzer inlet valve 70 is in the open configuration, and bypass valve 74 in the bypass line 30b is in the closed position.

Following usage in the dialyzer 11, spent fluid passes the control valve 72 to return to the system 10 through return line 30a and 30c with the bypass valve 74 is in the closed position. To ensure accurate operation of the balancing chambers 26, 28, as discussed below, spent fluid passes into the air separation chamber 36. From the air separation chamber 36, separated gases, and potentially fluid, are passed through return line 30d to the drain 34 by opening shutoff valves 76 and 80. Return fluid, from which the gases have been separated in the air separation chamber 36, may be pumped by flow pump 78 through return line 30e to one or both of the balance chambers 26, 28 through valves 63, 65. Leaving the balance chambers 26, 28 through valves 67, 69, respectively, the spent fluid is directed to a heat exchanger 38 and the drain 34 by way of return line 30f, overall flow to the drain 34 being controlled by shutoff valve 80. It will be appreciated that the heated spent fluid passing through the heat exchanger 38 may be used to heat the fluid flowing from the fluid source 22 to the hydroblock 24.

Operation of the balance chambers 26, 28 is known in the art. Within the balance chambers 26, 28, fresh fluid from the subsystem 12 passes along one side of the internal membranes, while spent fluid passes along the other side of the internal membranes. As will be appreciated by those of skill in the art, this pumping of spent fluid from line 30e along one side of the membrane with fresh fluid passing along the other side of the membrane results in a balanced provision of fluid from and to the dialyzer 11 during use.

Returning now to the structure and operation of the subsystem 12 for preparation of a salt solution, as explained in detail above, fluid flowing from the mainline 20b from the hydroblock 24 may be directed to the subsystem 12 by opening the control valve 54 and closing control valve 52 at adjacent junction 50 to provide flow to the subsystem line 56. To prepare the salt solution, fluid from the subsystem line 56 enters a container 82, which contains a powdered salt concentrate. The container 82 may be of any appropriate design, and may include a so-called bi-bag, which is a collapsible, replaceable bag that encloses the powdered salt concentrate.

As utilized in this disclosure, the term "container" 82 will be used to designate any or all of a rigid container, semiflexible container, or a bi-bag.

Figure 3:
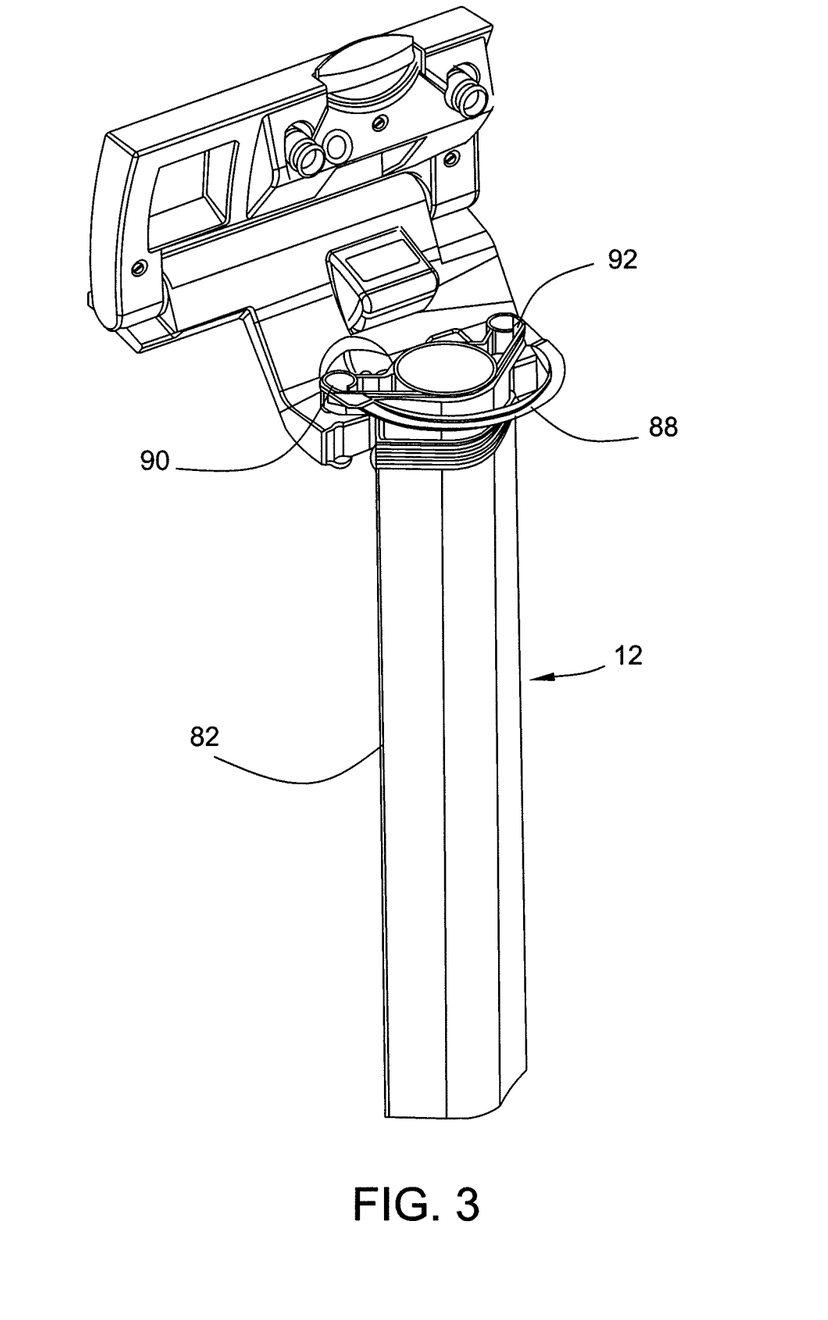
FIG. 3 is a representative drawing of an embodiment of a container having a powdered salt concentrate that can be used in the method and system of the present invention.

An example of a container 82 in accordance with the disclosed method is shown in FIG. 3. In this view, a protective cover has been removed to reveal the components of the container 82. The container 82 may be coupled to the subsystem 12 by any appropriate arrangement. In the illustrated embodiment, the container 82 is coupled to the subsystem 12 by a connector 88 having an inlet 90 and an outlet 92. As illustrated, the container 82 contains a dry powdered salt concentrate for use in preparation of a salt solution of a dialysate mixture.

Figure 4:
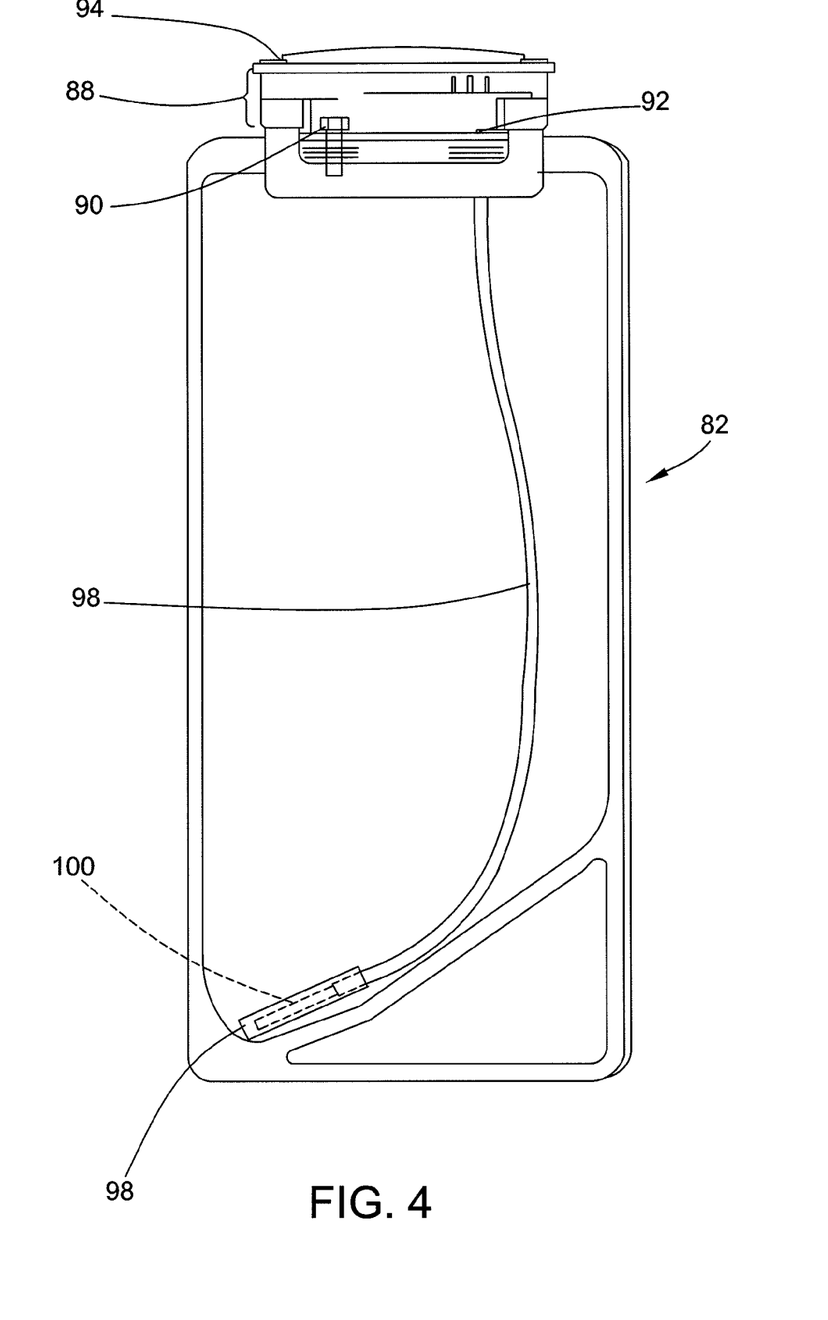
FIG. 4 is a partially cross-sectioned view of an embodiment of a container having a powdered salt concentrate that can be use in the method and system of the present invention.

FIG. 4 shows a partially cross-sectioned view of a container 82 having a protective cover 94 in place. A connector 88 may be utilized to couple the container 82 to the system 10. In order to allow the entry of fluid into and the removal of the salt solution from the container 82, an inlet 90 and an outlet 92 are provided. Although the inlet 90 and outlet 92 are shown in an upper portion of the container 82, the inlet 90 and outlet 92 may be alternately disposed, so long at the requisite mixing is obtained as provided by the disclosed method. For example, the inlet may be disposed in a lower portion of the container 82 to allow the fluid to be injected upward into the container 82 to encourage agitation to facilitate mixing.

In order to allow the mixed salt solution to be withdrawn from a container 82 that is not completely full, the outlet 92 originates below the level of fluid in the container 82. In the illustrated embodiment, a tube 96 having a lower opening 98 is fluidly coupled to the outlet 92 such that the opening 98 may be disposed in a lower portion of the container 82, that is, below the fluid level. To inhibit the intake of powdered salt that is not yet dissolved, a filter 100 may be disposed at the opening 98. The filter 100 may be made of any appropriate material, such as, for example, porous polyethylene.

The container 82 and the connector 88 may likewise be made of any appropriate material, and may be the same as or different from one another. By way of example only, either or both may be made of high density polyethylene or similar materials. The flexible container 82 may likewise be made of any suitable material, such as, by way of example only, a polyamide-polyethylene coextruded film.

The container 82 contains a dry form of one or more of any suitable salts used for preparation of dialysis solution. By way of example only, such suitable salts include sodium bicarbonate and sodium acetate. It will be understood by those of ordinary skill in the art that, when the powdered salt is sodium bicarbonate in particular, carbon dioxide will typically be generated from the initial contact between the fluid and the bicarbonate powder. Residual air is likewise often disposed within the container 82. As explained above, in order to provide proper removal of the salt solution from the container 82, it is necessary to maintain the opening 98 into the outlet 92 of the container 82 below the surface of the fluid contained therein. It will thus be appreciated that a reduction of gases disposed within the container 82 typically provides more space for the introduction of fluid.

In order to expel air from the subsystem 12, an air separation chamber 102 may be provided downstream the container 82. The air separation chamber 102, which is fluidly connected to the container 82 by the subsystem line 56, is designed to remove both air residually disposed within the container 82 and gases precipitating out of the bicarbonate solution when fluid is introduced to the powdered salt during operation of the subsystem 12.

In the illustrated embodiment, an air sensor 114 is provided on the air separation chamber 102. It will be appreciated that the air sensor 114 may be alternately disposed and may be of any appropriate design. For example, the air sensor 114 may be a two-pronged air detection probe located at the top of the air separation chamber 102 such that an electric current between the two prongs is detected when fluid fills the chamber 102 to at least the level of the prongs. Conversely, when there is air in the chamber 102, the air between the two prongs acts as an insulator and electric current does not flow.

Flow through the air separation chamber 102 is controlled by a control valve 104. If air is not detected in the air separation chamber 102, the control valve 104 is closed, the solution proceeds through subsystem line 108, advanced by a pump 110 to rejoin the mainline 20c at junction 58. The solution is then passed on to the balance chambers 26, 28 and to the mainline 20d for delivery to the dialyzer 11.

Conversely, if the air sensor 114 detects air in the air separation chamber 102, the control valve 104 is opened, and air is vented from the air separation chamber 102 through a degassing line 106 before rejoining the mainline 20c at junction 60. Upon rejoining the mainline 20c, the gas is passed to the balance chambers 26, 28 and to mainline 20d; with dialyzer valves 70 and 72 closed, the gas travels through return lines 30b and 30c, through air separation chamber 36, as explained above, before being expelled to the drain 34 through line 30d.

While it is known to withdraw air from the container 82 by way of a vacuum prior to introduction of fluid to the powdered salt, the disclosed method does not utilize such a vacuum to remove all of the gas from the container 82 before the introduction of fluid, as in the prior art. Rather, the disclosed method provides the desired layer of fluid over the powdered salt in the container by minimizing air in the container 82 after the introduction of fluid thereto. The disclosed method will be explained first with reference to the basic structure for performing the claimed method (see FIG. 5), and second with regard to the more detailed commercial embodiment of the system discussed above (see FIG. 2). Following these explanations, the operations of the respective systems by way of a controller are discussed.

Figure 5:
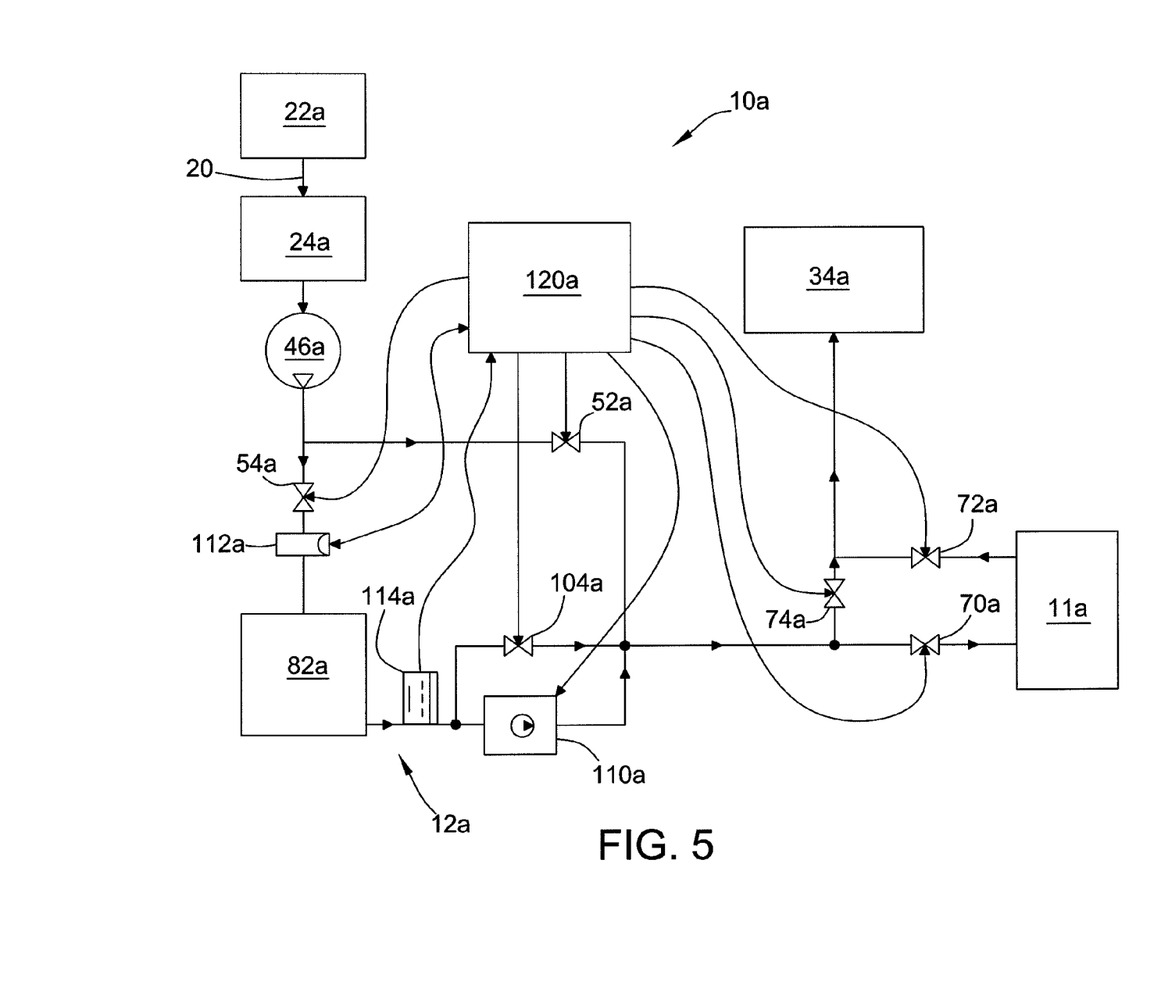
FIG. 5 is a schematic diagram of an embodiment of a system for the production and discharge of a liquid hemodialysis concentrate for use in a dialysis apparatus.

Turning first to FIG. 5, there is illustrated a system 10a for providing dialysate to a dialyzer 11a. For ease of understanding, the same reference numerals followed by the letter "a" are generally utilized to designate similar structures, with the exception of mainline 20, for which no modifier is utilized.

A mainline 20 fluidly couples a fluid source 22a, a subsystem 12a for the preparation of a salt solution, a drain 34a, and the dialyzer 11a. The subsystem 12a includes a container 82a which includes a powdered salt. A pump 46a pumps fluid passing through a heater and deaerator 24 from the fluid source 22a to container 82a or to mainline 20c, depending upon which of valves 54a, 52a is open. When valve 54a is open and valve 52a is closed, fluid is directed to the container 82a. Conversely, when valve 52a is open and valve 54a is closed, fluid from the pump 46a bypasses the subsystem 12a entirely.

According to the disclosed method, with valve 54a open, valve 104a closed, and pump 110a disabled, the pump 46a pumps fluid into the container 82a until the pressure within the container 82a reaches a specified, first pressure level. In the arrangement of FIG. 5, valve 54a periodically closes to allow a pressure sensor 112a to read the pressure within the line and container 82a. When the detected pressure reaches the specified, first pressure level, a flushing step is initiated by opening the downstream valve 104a. In the flushing step, the salt solution is then pushed from the container 82a while adequate additional fluid is introduced to the container 82a to maintain the specified pressure. This rapid flushing results in the expulsion of both the aqueous salt solution and gas.

During the flushing step, the valves 70a, 72a to and from the dialyzer 11a are closed to isolate the dialyzer 11a from the remainder of the system 10a. With valve 104a open and valve 52a closed, the fluid and expelled gas are directed through open bypass valve 74a to the drain 34a. During this flushing step, the pump 46c continues to provide fluid to the container 82a to maintain the pressure in the container 82a at the first pressure level.

The flushing step continues for either a preset period of time or until such time as gas is no longer detected in the expelled fluid, as by an air sensor 114a, for example, for a given period of time. The required flush time depends upon the volume of powdered salt disposed within the container 82a, greater amounts of solution requiring a more lengthy flush time period.

As discussed above, while the valves of the illustrated embodiment are simple two position shut off valves, alternate arrangements are envisioned. By way of example only valves 70a and 74a could be replaced with a three position valve that shuts off flow entirely, directs flow to the dialyzer, or directs flow to the drain 34a.

When the flushing step is completed, the valve 74a is closed to direct flow to the dialyzer inlet valve 70a as the container 82a begins normal operation at a second, lower operating pressure. During normal operation, the container 82a is filled with fluid as necessary to maintain the lower operating pressure, as the resultant fluid is directed to the dialyzer 11a.

The disclosed process of rapidly and immediately pushing fluid through the bag reduces the amount of gas that vents into the top of the container 82a, and, instead, pushes the gas out of the bottom of the container 82a in the flushing step. The expelled gas includes both residual gases in the container and the powdered salt, as well as carbon dioxide generated when fluid first makes contact with the powdered salt. It will be appreciated that the resultant reduction in gas within the bag provides additional room for the layer of fluid over the powdered salt.

The differences between the first pressure, that is, the flush pressure, and the second pressure, that is, the normal operation pressure, may be as appropriate to obtain the desired results. In an embodiment, the pressure in the container 82a during the flushing step can be raised anywhere from two to five fold over the operating pressure of the system, depending on the type of container and system. In an embodiment, the container 82a is pressurized in range between about 0.5 to 5 times the operating pressure, preferably between about 1 to 4 times the operating pressure, more preferably between about 1.5 to 3 times the operating pressure. In another embodiment, the pressure in the container 82a is maintained at about 2 times the operating pressure during the flushing step.

By way of example only, the fluid and trapped gases may be flushed from the system for a period of time ranging from 5 seconds to 5 minutes, depending upon aspects of the arrangement, including, for example, the volume of the container 82a and the amount of powdered salt contained therein. In various embodiments, the flushing step can last anywhere from 10 seconds to 2 minutes, 30 seconds to 2 minutes, 20 to 60 seconds, or about 30 seconds.

It will be appreciated that the system 10a may include additional fluid lines and components, such as, by way of example only, one or more of the components illustrated in FIG. 2 and explained in more detail above. Referring to FIG. 2, with valve 54 open and valve 52 closed at junction 50, the pump 46 moves fluid from the fluid source 22 through mainline 20b and subsystem line 56 to the container 82. With valve 104 closed and pump 110 disabled, pressure rises within the container 82 as fluid continues to be pumped into the container 82 by pump 46. When the pressure within the container 82 reaches a preset first pressure level, as measured by the pressure sensor 112, valve 104 is opened to initiate flushing of salt solution and gases from the container 82. The salt solution and entrained gases are then pushed from the container 82 in the flushing step, while the pump 46 provides additional fluid adequate to maintain the specified pressure within the container 82.

In the embodiment of FIG. 2, the flushed solution and gas enter the air separation chamber 102. Upon opening valve 104, the gas and flushed solution from the air separation chamber 102 flow through valve 104 and degassing line 106 to junction 60, where it rejoins the mainline 20c. The gas and flushed solution then proceed through one or both of valves 62, 64 into one or both of the balance chambers 26, 28, and out of one or both of valves 66, 68 to mainline 20d.

With the dialyzer 11 isolated from the system 10 by closed input and outlet valves 70, 72, and with bypass line 30b and valve 74 open, the expelled fluids and gas pass through return line 30c to air separation chamber 36. In air separation chamber 36, while a portion of the fluid may be separated from the gases, the gases and potentially fluid are directed through open valve 76 to return line 30d and open valve 80 to the drain 34. During this flushing step, or during the subsequent recovery step, pump 78 may pump the separated fluid within the air separation chamber 36 through return line 30e to one or both of the balance chambers 26, 28 through valves 63, 65. From the balance chambers 26, 28, the fluid moves through open valves 67, 69 to an optional heat exchanger 38, on through open valve 80 to the drain 34.

In an embodiment, the pressure in the container 82 can range between about 10 mmHg and 500 mmHg, preferably between about 50 mmHg and 300 mmHg, and more preferably between about 100 mmHg and 200 mmHg. By way of example only, the container 82 may be maintained at 150 mmHg, while the operating pressure of the arrangement is on the order of 90 mmHg.

In order to detect when air is no longer present in the fluid entering the air separation chamber 36, the air separation chamber 36 may include an air sensor 116 similar to the air sensor 114 of the air separation chamber 102. Although the air sensors 114, 116 are provided on the air separation chamber 102 and air separation chamber 36, they may be alternately disposed or additional sensors may be provided. At the conclusion of a set time period, or when gas is no longer detected by either one or both of the air sensors 114, 116, the flushing step may be discontinued, and the pressure within the container 82 reduced to a regular system operating pressure, as measured by the pressure sensor 112 or other appropriate sensor.

During this recovery step, pump 78 may be engaged to pump any fluids accumulated in the air separation chamber 36 to the drain. When switching over to regular operation, pump 110 may be engaged to pump salt solution to join mainline 20c at junction 58, and the valve 104 may be closed until such time as air is again detected by the air sensor 114. At this time, the bypass valve 74 is closed to direct flow to the dialyzer 11, and the valves 70, 72 may be reopened as appropriate to direct flow to and from the dialyzer 11. During regular operation of the system, the pump 46 is operated to maintain a desired system operating pressure; this second pressure in the container 82 is lower than the first pressure utilized in the flushing step of the process.

During regular operation, the air separation chamber 102 separates gas from fluid in the salt solution progressing to the dialyzer 11, while the air separation chamber 36 separates gas from spent fluid returning from the dialyzer 11. It will be appreciated that this elimination of the gases in the fluids flowing to and from the dialyzer 11 facilitates efficient and accurate operation of the balancing chambers 26, 28 during regular operation of the system 10.

As with the process explained with regard to FIG. 5, the disclosed process of rapidly and immediately pushing fluid through the container 82 in the system 10 of FIG. 2 reduces the amount of gas that vents into the top of the container 82, and, instead, pushes the gas out of the outlet 92 of the container 82 in the flushing process.

The system 10 may include one or more controllers, which are capable of activating one or more of the pumps 46, 110, 78, and/or one or more of the valves 42, 52, 54, 104, 62-70, 72, 74, 76, 80, and/or receiving input from pressure sensors 112 and/or air sensors 114, 116. For the purposes of this disclosure, we refer to only one controller, although it will be appreciated that multiple controllers may be provided. The controller may be of any appropriate design, such as, for example, a Microchip PIC 18F6410, although an alternate arrangement may be provided.

Returning to FIG. 5, the controller 120a receives input from the pressure and air sensors 112a and 114a, and directs the actuation/operation of the pumps 46a, 110a and valves 54a, 52a, 104a, 70a, 72a, 74a. In operation, the controller 120 directs the closure of valves 52a, 70a, 72a, 104a, the opening of valves 54a, 74a, and the disengagement of pump 110a. The controller 120a then directs the pump 46a to pump fluid from the fluid source 22a to the container 82a. When the reading received from the pressure sensor 112a reaches a preset first pressure, the controller 120a directs the opening of the valve 104a, at which time, fluid and gas from the container 82a is directed through the valves 104a, 74a to the drain 34a. During this time, the controller 120a directs the continued operation of the pump 46a at a speed sufficient to maintain the preset first pressure at pressure sensor 112a. If the pressure falls below the preset first pressure, the controller 120a maintain valve 54a in the open position to allow the pump 46a to continue filling the container 82; conversely, if the pressure is above the preset first pressure, the controller 120a directs valve 54a to remain closed until such time as the pressure as measured by the pressure sensor 112a again matches the preset first pressure.

When the controller 120a receives a reading of no air from the air sensor 114a for a set period, the controller 120a causes the system 10a to operate under regular operation. That is, the controller 120a directs valves 104a, 74a to close and valves 70a, 72a to open, and directs the engagement of pump 110a to cause the salt solution to flow to the dialyzer 11a. During regular operation, the controller 120a maintains a desired second, operating pressure, as measured by the pressure sensor 112a, the second, operating pressure being lower than the preset first pressure. As indicated above, the control of the pressure within the container 82 may be established by the opening and closing of valve 54a. In alternate embodiments of the arrangements shown in both FIGS. 2 and 5, however, control of the pressure within the container 82 may be established by reductions and increases in the speed of the pump 46a/46, in conjunction with or separate from the opening and closing of valve 54a/54 and/or valve 52a/52.

Referring to the embodiment of FIG. 2, a similar arrangement may be provided for operation of a controller. In various embodiments, the controller may receive input from pressure and air sensors 112, 114, 116, and may direct the operation of any or all of pumps 46, 110, 78 and any or all of valves 42, 52, 54, 104, 62-70, 72, 74, 76, 80.

By way of example of one such manner of operation of the controller, in a first step, the pump 110 is disabled, valves 104, 52 are closed, and valve 54 is opened, and the dialyzer 11 is isolated by closing valves 70, 72 and opening the bypass valve 74. In the balance chambers, valves 62 and 65-69 are opened.

The controller opens valve 54 to allow pump 46 to pump fluid into the container 82. When the pressure sensor 112 indicates that the desired, first pressure has been reached, the controller causes valves 104, 76 and 80 to be opened to flush gas and fluid through the container outlet through the air separation chamber 102, through degassing line 106 and mainline 20c, and through the balance chamber 26 to mainline 20d. The gas and fluid then proceeds through the bypass line 30b into the air separation chamber 36. From the air separation chamber 36, the gases proceed through return line 30d, through valve 80 to the drain 34. During this flushing step, the controller causes the opening and closing of the valve 54 in conjunction with the continued operation of the pump 46 to maintain the desired preset first pressure within the container 82 as measured by readings from the pressure sensor 112. After a preset period of time, for example, thirty seconds, the pump 78 may be activated to pump any accumulated fluids from the air separation chamber 36 through return line 30e and balance chamber 28 to the drain 34.

Once no air is detected at the air sensor 114 for a period of time, for example, two consecutive minutes, the controller causes valve 104 to close. Once the remainder of the fluid and gas pass through the bypass line 30b, bypass valve 74 is returned to a closed position, and the remainder of the valves are returned or set to a regular operating positions. The pump 110 is then activated, and the controller causes the valve 54 to open and close, such that the continued operation of the pump 46 provides a second, lower operating pressure at pressure sensor 112.

As explained above, the disclosed method may operate to reduce the residual gases and the gases precipitating from the solution without drawing a vacuum on the container 82. In the initial step, pressure is built in the substantially isolated container 82 until a first preset pressure is obtained. The flushing step is then initiated to flush gases, fluid, and entrained gases from the container to a drain. Either after a preset time or when gas is no longer sensed in the fluid from the container 82, the system is returned to a second, lower operating pressure, and the fluid from the container 82 is directed to the dialyzer 11. In this way, the level of air in the container 82 is effectively reduced to yield additional space for fluid. Accordingly, this reduction of air allows for effective operation of the container 82 in providing a salt solution for dialysis.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. In a system for use with a dialysis apparatus, a method for removing gases from a container having an inlet and an outlet, and containing a powdered salt concentrate, the method comprising the steps of:
   advancing fluid into the container through the inlet until a first pressure is reached to create a solution of fluid and salt concentrate;
   adding fluid into the container and flushing the solution through the outlet while maintaining the first pressure for a period of time to force gases trapped in the container through the outlet with the solution; and
   reducing the pressure in the container to a second pressure.

2. The method of claim 1 wherein the advancing step includes the step of using an inlet pump to advance fluid into the container.

3. The method of claim 1 further including monitoring the solution for the presence of gases.

4. The method of claim 3 further including comparing a monitored level of gas in the solution to a preset level.

5. The method of claim 3 wherein the reducing step includes reducing the pressure in the container to a second pressure when a monitored level of gas in the solution reaches an acceptable level.

6. The method of claim 1 further including the step of directing the solution to a drain.

7. The method of claim 1 wherein the powdered salt concentrate includes at least one of sodium bicarbonate and sodium acetate.

8. The method of claim 1 wherein the step of adding fluid, flushing the solution, and maintaining the first pressure includes maintaining the first pressure in the container at a level between about 0.5 and 5 times the second pressure.

9. The method of claim 1 wherein step of adding fluid, flushing the solution, and maintaining the first pressure includes maintaining the first pressure in the container at a level of about 2 times the second pressure.

10. The method of claim 1 further including the step of monitoring the pressure in the container with a pressure transducer.

11. The method of claim 1 further including the step of monitoring the pressure in the container with a pressure transducer located between a fluid source and the inlet to the container.

12. The method of claim 1 wherein the step of adding fluid, flushing the solution, and maintaining the first pressure includes withdrawing the solution via an outlet pump.

* * * * *